(12) United States Patent
Bleyer

(10) Patent No.: US 9,309,548 B2
(45) Date of Patent: Apr. 12, 2016

(54) PROCESS AND METHOD FOR IMPROVING THE ENZYMATIC HYDROLYSIS OF LIGNOCELLULOSIC BIOMASS BY ADDITION OF HYDROTHERMALLY TREATED STILLAGE

(71) Applicant: James Robert Bleyer, Maumee, OH (US)

(72) Inventor: James Robert Bleyer, Maumee, OH (US)

(73) Assignee: Valicor, Inc, Dexter ( * ) Notice: Subject to any disclaimer, the term of this patent is extended or adjusted under 35 U.S.C. 154(b) by 0 days.

(21) Appl. No.: 14/215,425

(22) Filed: Mar. 17, 2014

(65) Prior Publication Data

US 2014/0273108 A1 Sep. 18, 2014

Related U.S. Application Data

(60) Provisional application No. 61/788,977, filed on Mar. 15, 2013.

(51) Int. Cl.
*C12P 19/14* (2006.01)
*C12P 7/10* (2006.01)

(52) U.S. Cl.
CPC . *C12P 19/14* (2013.01); *C12P 7/10* (2013.01); *C12P 2201/00* (2013.01); *C12P 2203/00* (2013.01)

(58) Field of Classification Search
None
See application file for complete search history.

(56) References Cited

U.S. PATENT DOCUMENTS

2007/0037259 A1* 2/2007 Hennessey et al. ........... 435/105
2008/0299632 A1* 12/2008 Winsness et al. ............. 435/165

OTHER PUBLICATIONS

Kumar R et al. Effect of Additives on the Digestibility of Corn Stover Solids Following Pretreatment by Leading Technologies. 2009. Biotechnology and Bioengineering. vol. 102, No. 6. 1544-1557.*

* cited by examiner

*Primary Examiner* — David J Steadman
*Assistant Examiner* — Paul Holland
(74) *Attorney, Agent, or Firm* — Kohn & Associates, PLLC

(57) ABSTRACT

A method of producing hydrolysate from cellulosic material by adding hydrothermally treated stillage or a fraction thereof to cellulosic material, treating the mixture of hydrothermally treated stillage and cellulosic material with at least one hydrolyzing enzyme, and hydrolyzing and converting complex carbohydrates in the cellulosic material. The hydrolysate produced by the method. Ethanol, organic acids, and organism metabolites produced by the method. Biomass produced by the method. A method of increasing sugar production rate and yield of sugars from cellulosic material by adding hydrothermally treated stillage or a fraction thereof to cellulosic material, treating the mixture of hydrothermally treated stillage and cellulosic material with at least one hydrolyzing enzyme, and hydrolyzing complex carbohydrates in the cellulosic material and forming sugars.

25 Claims, 4 Drawing Sheets

PROCESS AND METHOD FOR IMPROVING THE ENZYMATIC HYDROLYSIS OF LIGNOCELLULOSIC BIOMASS BY ADDITION OF HYDROTHERMALLY TREATED STILLAGE

BACKGROUND OF THE INVENTION

1. Technical Field

The present invention relates to methods of improved enzymatic hydrolysis of cellulosic biomass by addition of hydrothermally treated stillage or a fraction thereof derived from a dry-grind ethanol process.

2. Background Art

Ethanol is an important component of liquid motor fuel supply. It is used as an oxygenate, octane booster and extender in gasoline. It is typically blended with gasoline to a concentration of 10% (E-10) or 85% (E-85). In the United States, ethanol is primarily made from sugars derived from corn starch. Cellulosic materials, such as wheat straw, grasses, corn stover (the leaves and stalks that remain after corn harvest) and corn cobs, silage, wood chips, and forest trimmings, are now being used as an alternative to corn starch to produce ethanol. Additionally, corn kernel fiber is also being considered as a feedstock. Cellulosic material is more abundant than corn and ethanol produced from such material has a greater greenhouse reduction. The EPA has called for 16 billion gallons of ethanol to be produced from cellulosic sugars by 2022.

Cellulosic materials are composed of carbohydrate polymers (celluloses) and aromatic polymers (lignin). The sugars of the carbohydrate polymers are tightly bound to the lignin. In the production of ethanol, the sugars are necessary for fermentation and must be extracted from the lignin.

One method of extracting these sugars in the cellulosic materials is enzymatic hydrolysis. While this is currently the most promising technology, it is not cost effective. Enzymatic hydrolysis requires high doses of expensive enzymes and produces relatively low sugar yields. While costs of enzymes have come down over the years, it remains a first order cost.

Methods have been employed to improve the economics of biomass enzymatic hydrolysis. A major improvement in the process economics can be realized by the effective pre-treatment of the cellulosic materials to dissolve or disrupt the lignin structure. This improves enzyme access to the cellulosic components and enhances enzymatic activity. Many pre-treatment methods have been investigated and have been extensively reviewed in the literature (V. B. Agbor et al./ Biotechnology Advances 29 (2011) 675-685). Pre-treatment methods include liquid hot water, steam explosion, ammonia fiber expansion (AFEX), aqueous ammonia treatment, ionic liquid fractionation, alkali treatment, ionic liquids, Organo-Solv process, dilute acid treatment, alkaline peroxide treatment, wet air oxidation, and low temperature steep delignification.

Other efforts to improve the economics of enzymatic hydrolysis focus on reduction and recycle of the enzymes.

U.S. Pat. No. 8,367,378 to Balan, et al. (assigned to Michigan State University) discloses a process for improving the enzymatic hydrolysis of ammonia pre-treated biomass by the addition of thin stillage or a clarified liquid portion of thin stillage. Balan, et al. does not teach or suggest improved enzymatic hydrolysis by the addition of clarified, hydrothermally treated stillage to pre-treated cellulosic biomass.

U.S. Patent Application Publication No. 2012/0244591 to T. Brotherson (assigned to Quad County Corn Processors) discloses a process to produce ethanol from the cellulose and hemicellulose present in the fiber fraction of whole stillage. The stillage is heated and acidified as a pre-treatment prior to addition of hydrolyzing enzymes. This application neither teaches nor suggests any benefit of stillage to the enzymatic hydrolysis step but is rather focused on utilization of the fiber in stillage as an additional source of sugars for ethanol production.

PCT/US2012/021731 to Narendranath, et al. (assigned to POET LLC) discloses a process for treating cellulosic biomass including the addition of a clarified thin stillage stream to the enzymatic hydrolysis step. Narendranath, et al. disclose that addition of either a thin stillage composition or anaerobic digestion effluent, each having substantially reduced insoluble solids, to the enzymatic hydrolysis step improves release of sugar from pre-treated cellulosic biomass and further improves fermentation of the hydrolysate to ethanol. Narendranath, et al. do not teach or suggest improved enzymatic hydrolysis by the addition of clarified, hydrothermally treated stillage to pre-treated cellulosic biomass.

U.S. Patent Application Publication No. 2010/0159552 to R. Benson and R. Benech (assigned to Greenfield Ethanol) discloses a process for improved fermentation of pre-treated cellulosic biomass by addition of a stillage residue stream. Benson and Benech do not teach or suggest the addition of a stillage residue stream to the enzymatic hydrolysis step; nor do they teach or suggest that hydrothermal treatment of the stillage stream affords an improved hydrolysis media.

There remains a need for a cost effective method of enzymatic hydrolysis of cellulosic materials in order to produce ethanol from cellulosic material.

SUMMARY OF THE INVENTION

The present invention provides for a method of producing hydrolysate from cellulosic material by adding hydrothermally treated stillage or a fraction thereof to the cellulosic material, treating the mixture of hydrothermally treated stillage and cellulosic material with at least one hydrolyzing enzyme, and hydrolyzing and converting complex carbohydrates in the cellulosic material.

The present invention further provides for the hydrolysate formed by hydrolyzing the complex carbohydrates in the cellulosic material in the presence of hydrothermally treated stillage.

The present invention provides for ethanol, organic acids, and metabolites produced by fermenting the hydrolysate.

The present invention also provides for biomass grown from the hydrolysate as a carbon source.

The present invention provides for a method of increasing sugar production rate and yield of sugars from cellulosic material by adding hydrothermally treated stillage or a fraction thereof to cellulosic material, treating the mixture of hydrothermally treated stillage and cellulosic material with at least one hydrolyzing enzyme, and converting complex carbohydrates to sugars.

DESCRIPTION OF THE DRAWINGS

Other advantages of the present invention are readily appreciated as the same becomes better understood by reference to the following detailed description when considered in connection with the accompanying drawings wherein.

DETAILED DESCRIPTION OF THE INVENTION

Figure 1:
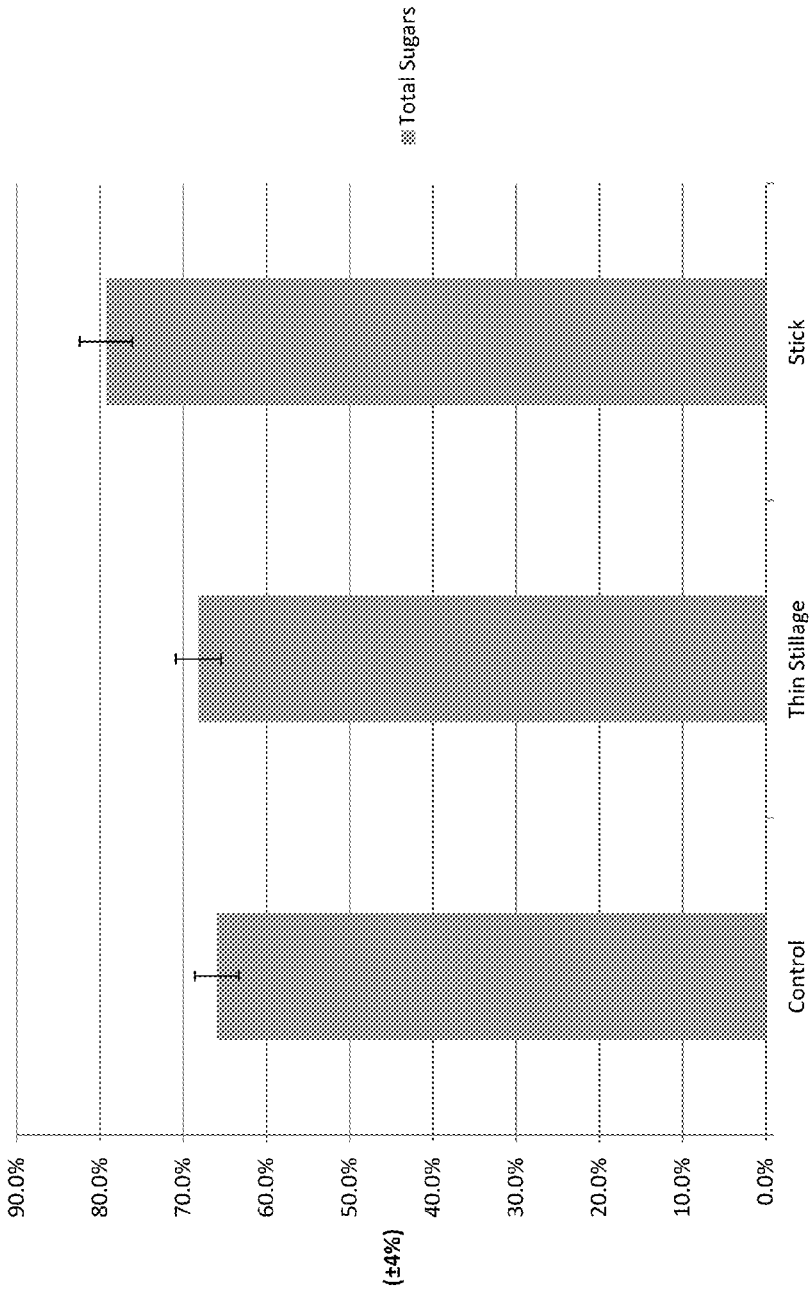
FIG. 1 is a graph of results of straw pulp hydrolysis with a control, thin stillage, and stickwater addition.

The present invention generally provides for methods of enhancing the effectiveness of enzymatic hydrolysis of cellulosic materials to produce hydrolysate by adding hydrothermally treated stillage or a fraction thereof from a corn-ethanol plant. The addition of hydrothermally treated stillage increases the rate of sugar produced as well as the yield of sugars from the cellulosic material. The sugars can then be fermented to ethanol, used as a carbon source to grow biomass, or used as a carbon source to produce organic acids and other metabolites.

More specifically, the present invention provides for a method of producing hydrolysate from cellulosic material by adding hydrothermally treated stillage or a fraction thereof to cellulosic material, and treating the mixture of the cellulosic material and hydrothermally treated stillage with at least one hydrolyzing enzyme, and hydrolyzing and converting complex carbohydrates in the cellulosic material.

The hydrothermally treated stillage is produced by heating stillage to a temperature from 220 degrees F. to 350 degrees F., for 3 to 90 minutes. The stillage can be pressurized during heating at or above the saturation pressure of the stillage. The stillage can be cooled below 212 degrees F. after the heating step. The physicochemical changes imparted by hydrothermal treatment, including enablement of facile separation of stillage suspended solids, and a significant increase of the soluble protein concentration in heat treated stillage versus thin stillage are described in U.S. Patent Application Publication Nos. 2013/0344554 and 2014/0017728 assigned to Valicor Inc.

"Cellulosic biomass" as used herein, also called lignocellulosic biomass or cellulosic material, is a complex composite material consisting of cellulose and hemicellulose (structural carbohydrates), which can be bonded to lignin in plant cell walls. For simplification, the term cellulosic biomass is used as plant tissues can contain widely varying amounts of lignin including virtually no lignin. Within corn, for example, levels of lignin are found at approximately 34% in whole stalks, 6% in cobs and only 0.2% in kernels. (Corn: Chemistry and Technology, S. A. Watson and P. E. Ramstad eds., American Association of Cereal Chemists, Inc., $4^{th}$ printing, 1999.)

"Hydrolysate" as used herein, refers to the mixture of 5-carbon and 6-carbon saccharides including monosaccharides, disaccharides, and oligosaccharides (typically 3-9 monosaccharide units) produced as the result of treatment of the complex carbohydrates of cellulosic material with one or more hydrolyzing enzymes. Based on the efficiency of pretreatment and degree of enzymatic hydrolysis, hydrolysate can contain higher polysaccharides and residual non-hydrolyzed complex carbohydrates. Hydrolysate can also contain lignin, proteins, amino acids, short and long chain fatty acids, lipids, salts and other components present in the original and pre-treated cellulosic material.

"Sugar" as used herein and per convention, refers to plant saccharides including simple sugars (monosaccharides and disaccharides), and oligosaccharides.

"Stillage" as used herein, refers to a cloudy liquid produced during ethanol fermentation that includes solids that are not fermentable, solubles, oils, organic acids, salts, proteins, and various other components. The stillage used in the heating step can be whole stillage, thick stillage, or thin stillage. Whole stillage can contain approximately 8-10% suspended solids (11-13% total solids). Stillage with a solid content less than whole stillage and more than thin stillage is referred to as thick stillage. Thick stillage can have approximately 4 to 8% suspended solids. Thin stillage has suspended solids typically in the range of 1.5-3% (4.5-6% total solids). Thin stillage with 4% or less suspended solids can be used.

"Stickwater" as used herein refers to a clarified stream derived from the hydrothermally treated stillage and having substantially less suspended solids than thin stillage, typically less than 1 wt % or less than 50% of the suspended solids in the mother liquor, and is mainly water and solubles. The stillage readily partitions into a high solids fraction and a stickwater fraction due to the hydrothermal treatment. Solids can also be removed or partitioned from the hydrothermally treated stillage to obtain the stickwater before adding to the cellulosic material, in a method/apparatus such as, but not limited to, decanting centrifuge, disc stack centrifuge, filtration, membrane filtration, dissolved air flotation, or a hydrocyclone. It should be understood that either the stickwater can be used in the present invention or the different types of hydrothermally treated stillage, and where one of these terms are referred to, the other can be used interchangeably.

It has been shown in the prior art that addition of soluble proteins to the enzymatic hydrolysis step can improve the overall release of sugars from pretreated cellulosic biomass [R. Kumar and C. Wyman, Biotechnology and Bioengineering, Vol. 102, No. 6, Apr. 15, 2009]. It is proposed that the added proteins serve to stabilize the hydrolyzing enzymes or otherwise compete with deleterious enzyme inhibitors.

The cellulosic material can also be pretreated according to various methods well known in the art. The purpose of pretreatment is to disrupt the lignin, cellulosic, and hemi-cellulosic matrix, thereby increasing the exposure of the carbohydrates to hydrolyzing enzymes in the hydrolysis step and improving the yield of sugars in the hydrolysate. Pretreatment methods include, but are not limited to, steam explosion, ammonia fiber expansion (AFEX), ionic liquid fractionation, dilute acid treatment, alkaline peroxide treatment, wet air oxidation, or low temperature steep delignification. Thus cellulosic hydrolysis can be enhanced by improved enzyme access to substrate due to pretreatment coupled with enzyme stabilization and inhibitor attenuation by soluble proteins in the hydrothermally treated stillage.

The cellulosic material can be any suitable material, such as, but not limited to, corn kernel fiber, dried distillers grains, wheat straw, grasses, corn stover and cobs, silage, wood chips and forest trimmings. The cellulosic material can further include sugar, starch, or combinations thereof.

The method can further include the step of fermenting the hydrolysate sugars into one or more of the following by a suitable organism: alcohols (e.g. methanol, ethanol, propanol, butanol or other alkyl alcohols), diols (e.g. 1,3-propanediol, 1,4-butanediol), organic acids (e.g. lactic, propionic, citric, succinic), proteins, vitamins and/or other organism metabolites.

The method can further include the step of concentrating, isolating, or removing sugars from the hydrolysate. The hydrolysate can be concentrated by evaporation, filtration, membrane filtration, reverse osmosis, or precipitation. The sugars can be removed simultaneously with the enzymatic hydrolosis (i.e. during the step of treating the mixture of the cellulosic material and hydrothermally treated stillage with at least one hydrolyzing enzyme).

In one embodiment, whole stillage from the beer column of a conventional dry grind ethanol facility is separated into distiller's wet grains (DWG) and thin stillage. The thin stillage is hydrothermally treated above 220 degrees F., cooled to less than 212 degrees F. and separated to produce distiller's corn oil, a high solids fraction and low suspended solids stickwater fraction. Corn stover is ground and pre-treated by low temperature steep delignification or other cellulosic pre-treatment method to disrupt the cellulosic matrix of the corn fiber. Stickwater and suitable cellulose and hemi-cellulose digesting enzymes are added to the pre-treated corn stover and hydrolysis proceeds. A C5/C6 fermenting bacteria, fungi, or a yeast genetically modified to ferment C5 sugars as well as C6 sugars is added to the stickwater/hydrolysate mixture to convert the hydrolysate sugars to ethanol. Such modified yeast have been developed for example by Terranol A/S (Denmark) and Royal Dutch DSM.

The hydrolysate can additionally be co-fermented with sugars produced from a source such as, but not limited to, starch, sugar beets, cane sugar, sweet sorghum, other sugar sources, and combinations thereof. Furthermore, the ethanol produced by fermenting the hydrolysate can be added to ethanol produced by starch fermentation. The hydrolyzing step in the method and the fermenting step can occur simultaneously.

The method can also include the step of using the hydrolysate as a carbon source and growing biomass, such as, but not limited to, algae, fungi/yeast, or bacteria. For example, the oleaginous fungus *Mortierella isabellina* has been grown on rice hull hydrolysate, the fungal biomass being capable of accumulating large quantities of lipids that can serve as feedstock for the production of biofuels. [C. Economou et al., Biores. Tech. 102(20), 9737-42, October 2011] Also, the hydrolyzing step in the method and the growing step can occur simultaneously.

The present invention further provides for the hydrolysate (sugars) formed by hydrolyzing the complex carbohydrates in the cellulosic material. The present invention provides for the ethanol, organic acids, and metabolites produced by fermenting the sugars as described above. The present invention also provides for the biomass grown as described above.

The present invention also provides for a method of increasing sugar production rate and yield of sugars from cellulosic material by adding hydrothermally treated stillage or a fraction thereof to cellulosic material, treating the mixture of hydrothermally treated stillage and cellulosic material with at least one hydrolyzing enzyme, and hydrolyzing complex carbohydrates in the cellulosic material and forming sugars. Each of these steps is described above. The method is able to increase the sugar production rate and yield from cellulosic material compared to prior art processes due to the addition of the hydrothermally treated stillage. The addition of soluble proteins enhances enzymatic hydrolysis. As shown in U.S. Patent Application Publication Nos. 2013/0344554 and 2014/0017728, the amount of soluble proteins is higher in hydrothermally treated stillage.

The invention is further described in detail by reference to the following experimental examples. This example is provided for the purpose of illustration only, and are is not intended to be limiting unless otherwise specified. Thus, the invention should in no way be construed as being limited to the following examples, but rather, should be construed to encompass any and all variations which become evident as a result of the teaching provided herein.

Example 1

Thin Stillage was collected from a corn ethanol plant. Part of the thin stillage was used for addition to the hydrolysis without hydrothermal treatment. The remaining thin stillage was used as feedstock for the hydrothermal treatment process. The thin stillage was heated to 280 F for 40 minutes, cooled to 180 F, and decanted by means of quiescent decantation. Stickwater was collected from the decantation step.

Corn Stover was collected and pre-treated by low temperature steep delignification (LTSD), a proprietary pre-treatment developed by Bio-Process Innovation, Inc. (226 N 500 W, West Lafayette, Ind. (47906). Samples for enzymatic hydrolysis were made up to 150 g total weight in 250 ml flasks. Dried, pre-treated corn stover (pulp) was added so that the total pulp solids were 5.3%.

1) For the control, 32 g of de-lignified stover pulp at 23% solids was mixed with 118 ml $H_2O$ and adjusted to pH 5 with potassium phosphate buffer.

2) The two variable samples were made up with 32 g wet basis stover pulp, 15 ml 'thin stillage' or 'stickwater' and 103 ml $H_2O$ and adjusted to pH 5 with potassium phosphate buffer.

3) 0.15 g of Novozymes Cellic® CTec2 cellulase was added to each flask corresponding to 2% w/w cellulase/biomass dry basis and the samples were put in an incubator shaker set at 50° C. for 48 hours. The concentration of enzyme was chosen to be at the low end of suggested use levels (3 to 5%) as per Appendix 1 to allow a better perspective on the enhancing effects of the additives.

4) The experiments were carried out in triplicate.

After 48 hours, the reaction was stopped by putting the flasks in the refrigerator, and carbohydrates were measured by and HPLC with refractive index.

Results

Sugars and residual total solids were measured in all of the flasks after 48 hours (shown in TABLE 1). Control Sample 1 was found to be contaminated and is not included in the report.

TABLE 1

Released Sugars from Pulp after 48 hours*

Sugar Recovery as weight % of total substrate Treatment

| | Control | | Thin Stillage | | | Stickwater | | |
|---|---|---|---|---|---|---|---|---|
| Sample id# | C2 | C2 | TS1 | TS2 | TS3 | SW1 | SW2 | SW3 |
| Glucose | 49.0% | 44.7% | 44.4% | 45.1% | 47.5% | 54.7% | 53.9% | 55.2% |
| Xylose | 20.6% | 18.4% | 21.6% | 25.5% | 20.5% | 26.3% | 24.2% | 23.5% |
| Total Glu + Xyl | 69.6% | 63.1% | 66.0% | 70.6% | 68.0% | 81.0% | 78.1% | 78.7% |
| Average Total Glu + | | 66.4% | | 68.2% | | | 79.3% | |

TABLE 1-continued

| Released Sugars from Pulp after 48 hours* | | | |
|---|---|---|---|
| Xyl for all samples in treatment | | | |
| Standard Deviation (% absolute) | 3.25% | 1.88% | 1.25% |
| Standard Deviation (% relative) | 4.90% | 2.76% | 1.58% |
| Avg. Hydrolysis Rate (wt %/hr) | 1.38 | 1.42 | 1.65 |

| Statistical Analysis (T-test) | | | |
|---|---|---|---|
| Comparison | TS vs Ctrl | SW vs Ctrl | SW vs TS |
| p-value (2 tail) | 0.578 | 0.017 | 0.002 |
| Statistically Different? | NO | YES | YES |

Discussion of Results

As per TABLE 1 and FIG. 1, there was not a statistically significant positive effect (p>>0.05) on the cellulase hydrolysis performance from using thin stillage. However, the "stickwater" showed a statistically significant positive effect (p<0.05) on the extent of enzyme hydrolysis of the pulp versus either the control or thin stillage. On average 79% of the pulp solids converted to sugars with "stickwater" versus 66% and 68% respectively for the control and thin stillage, representing about a 20% increase in sugars released within 48 hours. This was repeatable as variation among the sample treatments was typically less than 5% (relative).

Example 2

Effect of Time and Temperature on Soluble Protein in Hydrothermally Treated Stillage Procedures For the present example, a two factor statistical design of experiments (DOE) methodology was used to evaluate the effect of time and temperature on soluble protein in hydrothermally treated thin stillage. The central composite design (CCD) covered the time-temperature ranges of 4-116 minutes and 184 degrees F.-296 degrees F., with a center point at 60 minutes, 240 degrees F. replicated four times. Thin stillage obtained from a commercial ethanol plant was pumped from a well-stirred 5-gallon plastic container through a series of Plate and Frame Heat Exchangers (PHEs) into a stirred 1-gallon batch reactor. The PHEs heated the stillage to the target temperature and the jacketed reactor held the stillage for the prescribed residence time. The reactor pressure was maintained at the saturation pressure of the stillage. At the end of the prescribed residence time, the reactor contents were gravity drained into a clean 1-gallon plastic container, uniformly mixed and poured off into 1-L wide-mouth plastic bottles. The 1-liter bottles were centrifuged in a bottle centrifuge (Damon/IEC model EXD centrifuge, Needham Heights, Mass., USA; approx. 18 inch inside chamber diameter) by ramping to full speed (3100 rpm, 2714 G-sec), holding for 1 minute at full speed and ramping down. At the end of centrifugation, the typical top-to-bottom partitioning of material in a full 1-L bottle comprised about 1-2 cm of a floating oil emulsion, about 10 cm of stickwater, and about 1-1.5 cm of deposited solids. The oil and water layers from each 1-L bottle were carefully poured off, taking care not to disturb the deposited solids, into a 1.25 gallon bench-top gravity decanter (a clear plastic water container of dimensions 12.5 in. length×9 in. height×3 in. wide, set on its narrow face at about a 15 degree angle, and equipped with a low point drain valve). The oil and water layers were allowed to gravity separate in the bench-top decanter for 5 minutes after which the bottom stickwater phase was drained through the low-point valve, leaving a small volume of stickwater in the decanter so as to assure a stickwater sample containing no second phase oil. Finally the oil phase was drained from the bench-top decanter with a small amount of residual stickwater. The thin stillage feed and the resulting stickwater from each heat treatment condition were analyzed for soluble protein.

Methods of Analysis

Soluble protein was analyzed according to the "BCA" method of Smith et al. (Smith, P. K., et al. (1985). Measurement of protein using bicinchoninic acid. Anal Biochem 150: 76-85.)

Results and Discussion

Figure 2:
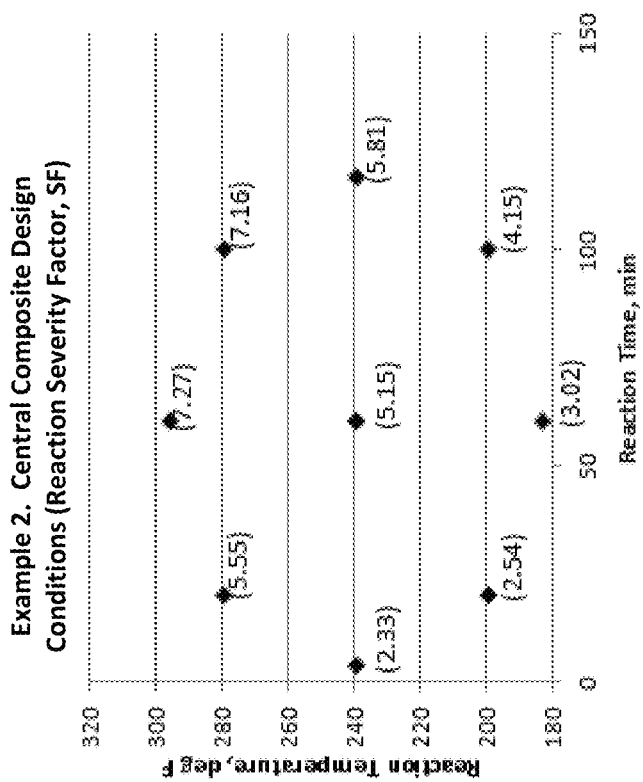
FIG. 2 is a graph showing central composite design conditions (reaction severity factor, SF)

The DOE run conditions are depicted in FIG. 2. In the area of biomass hydrothermal treatment and lignocellulosic pretreatment, the concept of reaction severity has been applied to account for the combined effects of time and temperature. Overend et al. (Phil. Trans. R. Soc. London A, (1987) 321: 523-536) developed the generalized severity parameter, $R_o$ shown below, where t is the reaction time and $\omega$ expresses the temperature influence and is related to the average activation energy for hydrolysis reactions. The reaction severity factor, SF, is taken as the natural logarithm of the generalized severity parameter and is a unit-less value (S. H. da Cruz et al., J Ind Microbiol Biotechnol (2012) 39:439-447).

$$Ro = \int_0^t \exp\left(\frac{T - Tref}{\omega}\right) dt \qquad \text{(FORMULA 1)}$$

which for an isothermal reaction becomes $$Ro = \exp\left(\frac{T - Tref}{\omega}\right) \times t \qquad \text{(FORMULA 2)}$$

$$SF = \ln(Ro) \qquad \text{(FORMULA 3)}$$

$T_{ref}$ was taken as 100 degrees C. (212 degrees F.) and a value of 14.75 was used herein as suggested by Overend et al. for aqueous/steam hydrolysis of biomass. Values for SF, the hydrothermal treatment run conditions and analytical results are given in TABLE 2.

TABLE 2

| Sample | Reaction Time, min | Reaction Temp, F. | Reaction Severity Factor, SF | Soluble BCA Protein, g/L |
|---|---|---|---|---|
| Thin Stillage (Feed) Stickwater Samples | n/a | n/a | 2.53* | 7.4 |
| 1** | 60 | 240 | 5.15 | 7.4 |
| 2a | 116 | 240 | 5.81 | 8.6 |
| 2b | 116 | 240 | 5.81 | 8.5 |
| 3 | 20 | 280 | 5.55 | 9.4 |
| 4 | 100 | 200 | 4.15 | 7.3 |
| 5 | 20 | 200 | 2.54 | 7.7 |
| 6** | 60 | 240 | 5.15 | 9.4 |
| 7** | 60 | 240 | 5.15 | 9.1 |
| 8a | 100 | 280 | 7.16 | 11.1 |
| 8b | 100 | 280 | 7.16 | 10.2 |
| 9 | 60 | 184 | 3.02 | 7.9 |
| 10 | 4 | 240 | 2.33 | 9.0 |
| 11 | 60 | 296 | 7.27 | 12.1 |
| 12** | 60 | 240 | 5.15 | 9.6 |
| Ctr Pt Avg | 60 | 240 | 5.15 | 7.9 |

*For comparison purposes, the time-temperature history and hence $R_{SF}$ for thin stillage was estimated by assuming 35 min at 185 degrees F. as a typical residence time and bottom temperature in the beer column.
**Center points of the DOE replicated four times.

Figure 3:
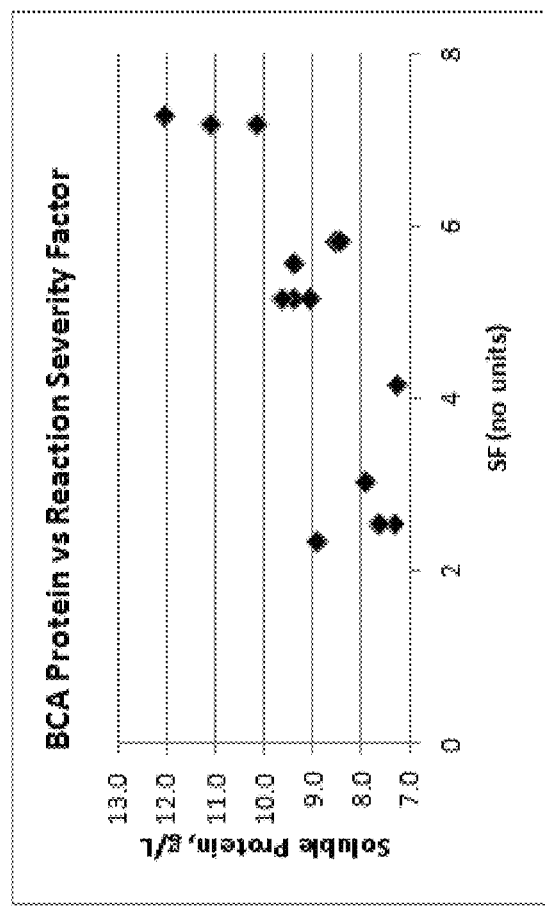
FIG. 3 is a graph showing BCA protein versus reaction severity factor.
Figure 4:
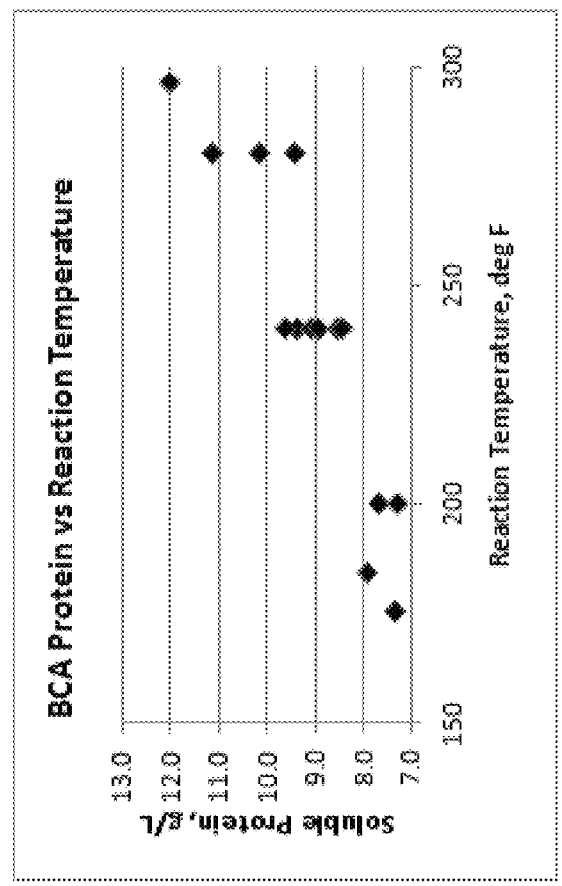
FIG. 4 is a graph showing BCA protein versus reaction temperature.

FIG. 3 shows a chart of the data from TABLE 2 plotted against the reaction severity factor, SF, while FIG. 4 shows a chart for the data plotted against reaction temperature. Although there is some scatter in the data, soluble protein clearly increases in stickwater with increasing reaction severity or temperature. It is believed that hydrolysis reactions are contributing to the observed increases. Soluble protein is consequently more available in hydrothermally treated stillage than in the mother liquor to stabilize cellulytic enzymes and attenuate enzyme inhibitors in a subsequent biomass enzymatic hydrolysis step. Therefore, stickwater can provide unique advantages of increasing sugar production rate and yield of sugars from cellulosic material when added thereto in a hydrolysis process.

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology, which has been used is intended to be in the nature of words of description rather than of limitation.

Obviously, many modifications and variations of the present invention are possible in light of the above teachings. It is, therefore, to be understood that within the scope of the appended claims, the invention can be practiced otherwise than as specifically described.

What is claimed is:

1. A method of producing hydrolysate from cellulosic material, comprising the steps of:
    adding hydrothermally treated stillage comprising soluble protein to cellulosic material to form a mixture;
    treating said mixture of hydrothermally treated stillage and cellulosic material with at least one hydrolyzing enzyme, wherein said soluble protein stabilizes and attenuates inhibition of said at least one hydrolyzing enzyme, and;
    allowing said at least one hydrolyzing enzyme to hydrolyze complex carbohydrates in said cellulosic material to form a hydrolysate comprising monosaccharides, disaccharides, and oligosaccharides, and wherein said hydrolysate comprises an increased sugar yield as compared to a cellulosic material not mixed with said hydrothermally treated stillage.

2. The method of claim 1, wherein said hydrothermally treated stillage is produced by heating stillage to a temperature of 220° F. to 350° F.

3. The method of claim 2, wherein said hydrothermally treated stillage is heated for 3 to 90 minutes.

4. The method of claim 2, wherein said hydrothermally treated stillage is pressurized at or above the saturation pressure of the stillage.

5. The method of claim 2, wherein after said heating, the hydrothermally treated stillage is cooled below 212° F.

6. The method of claim 1, wherein said hydrothermally treated stillage is selected from the group consisting of whole stillage, thick stillage, and thin stillage.

7. The method of claim 1, wherein solids are removed from said hydrothermally treated stillage prior to adding to the cellulosic material.

8. The method of claim 7, wherein said solids are removed by a method selected from the group consisting of decanting centrifuge, disc stack centrifuge, filtration, membrane filtration, dissolved air flotation, hydrocyclone, and combinations thereof.

9. The method of claim 1, wherein said cellulosic material is pre-treated to disrupt the matrix of lignin, cellulosic, and hemi-cellulosic material prior to said treating step.

10. The method of claim 9, wherein said pre-treatment is selected from the group consisting of steam explosion, liquid hot water, supercritical water, ammonia fiber expansion (AFEX), ionic liquid fractionation, dilute acid treatment, alkaline peroxide treatment, wet air oxidation, and low temperature steep delignification.

11. The method of claim 1, wherein said cellulosic material is selected from the group consisting of dried distillers grains, corn kernel fiber, wheat straw, grasses, corn stover, corn cobs, silage, bagasse, wood chips, forest trimmings, and combinations thereof.

12. The method of claim 11, wherein said cellulosic material further comprises a composition selected from the group consisting of sugars, starch, and combinations thereof.

13. The method of claim 1, further comprising a step of fermenting said hydrolysate into a fermentation product selected from the group consisting of ethanol, organic acids, organism metabolites, and combinations thereof.

14. The method of claim 13, wherein said hydrolysate is co-fermented with sugars produced from a sugar source.

15. The method of claim 14, wherein said sugar source is selected from the group consisting of starch, sugar beets, cane sugar, sweet sorghum, and combinations thereof.

16. The method of claim 13, wherein said fermentation product is added to a fermentation product produced from another sugar fermentation.

17. The method of claim 13, wherein said hydrolyzing and said fermenting occur simultaneously.

18. The method of claim 1, further comprising a step of using the hydrolysate as a carbon source for growing biomass.

19. The method of claim 18, wherein said biomass is selected from the group consisting of algae, fungi, yeast, bacteria, and combinations thereof.

20. The method of claim 18, wherein said hydrolyzing and said growing occur simultaneously.

21. A method of increasing sugar production rate and yield of sugars from cellulosic material, comprising the steps of:
adding hydrothermally treated stillage comprising soluble protein to cellulosic material to form a mixture;
treating said mixture of hydrothermally treated stillage and cellulosic material with at least one hydrolyzing enzyme, wherein said soluble protein stabilizes and attenuates inhibition of said at least on hydrolyzing enzyme, and;
allowing said at least one hydrolyzing enzyme to hydrolyze complex carbohydrates in said cellulosic material to form a hydrolysate comprising monosaccharides, disaccharides, and oligosaccharides, and wherein said hydrolysate comprises an increased sugar yield and sugar production rate as compared to a cellulosic material not mixed with said hydrothermally treated stillage.

22. The method of claim 1, further comprising a step of concentrating said hydrolysate.

23. The method of claim 22, wherein said hydrolysate is concentrated by a method selected from the group consisting of evaporation, filtration, membrane filtration, reverse osmosis, and precipitation.

24. The method of claim 1, further comprising a step of removing sugars from said hydrolysate.

25. The method of claim 24, wherein said removing sugars step occurs simultaneously with said treating step.

* * * * *